(12) United States Patent
Kim et al.

(10) Patent No.: US 12,037,375 B2
(45) Date of Patent: Jul. 16, 2024

(54) PROTEIN VARIANT AND COMPOSITION FOR TREATING NEURODEGENERATIVE DISEASE USING THE SAME

(71) Applicant: KOREA UNIVERSITY RESEARCH AND BUSINESS FOUNDATION, Seoul (KR)

(72) Inventors: Hugh Inkon Kim, Seoul (KR); Dongjoon Im, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 18/048,655

(22) Filed: Oct. 21, 2022

(65) Prior Publication Data

US 2023/0212242 A1 Jul. 6, 2023

(30) Foreign Application Priority Data

Dec. 30, 2021 (KR) .......... 10-2021-0192521
Mar. 31, 2022 (KR) .......... 10-2022-0040355

(51) Int. Cl.
*C07K 14/47* (2006.01)
*A23L 33/18* (2016.01)
*A61P 25/28* (2006.01)
*C12N 15/63* (2006.01)

(52) U.S. Cl.
CPC .......... *C07K 14/4711* (2013.01); *A23L 33/18* (2016.08); *A61P 25/28* (2018.01); *C12N 15/63* (2013.01)

(58) Field of Classification Search
CPC ...... C07K 14/4711; A23L 33/18; A61P 25/28; C12N 15/63
See application file for complete search history.

(56) References Cited

U.S. PATENT DOCUMENTS

2011/0092445 A1* 4/2011 Barghorn ............... C07K 16/18
514/21.1

OTHER PUBLICATIONS

Christine Wurth, Mutations that Reduce Aggregation of the Alzheimer's Ab42 Peptide: an Unbiased Search for the Sequence Determinants of Ab Amyloidogenesis, J. Mol. Biol. (2002) 319, 1279-1290.*

* cited by examiner

*Primary Examiner* — Julie Ha
*Assistant Examiner* — Erinne R Dabkowski
(74) *Attorney, Agent, or Firm* — Sughrue Mion, PLLC

(57) ABSTRACT

Disclosed are a novel protein variant for controlling fibrosis of amyloid beta and a composition for treating neurodegenerative diseases using the same.

7 Claims, 14 Drawing Sheets
Specification includes a Sequence Listing.

[FIG. 4]
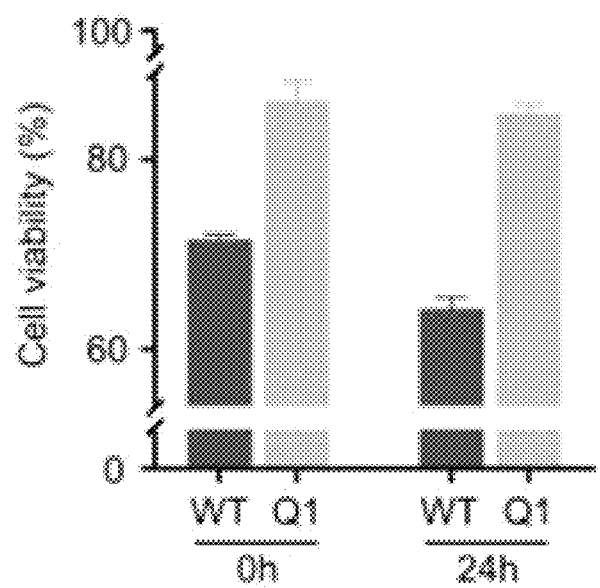

SEQUENCE LISTING

```
Sequence total quantity: 8
SEQ ID NO: 1            moltype = AA  length = 42
FEATURE                 Location/Qualifiers
REGION                  1..42
                        note = amyloid beta protein
source                  1..42
                        mol_type = protein
                        organism = synthetic construct
SEQUENCE: 1
DAEFRHDSGY EVHHQKLVFF AEDVGSNKGA IIGLMVGGVV IA                           42

SEQ ID NO: 2            moltype = AA  length = 42
FEATURE                 Location/Qualifiers
REGION                  1..42
                        note = F19N/I32N/L34N
source                  1..42
                        mol_type = protein
                        organism = synthetic construct
SEQUENCE: 2
DAEFRHDSGY EVHHQKLVNF AEDVGSNKGA INGNMVGGVV IA                           42

SEQ ID NO: 3            moltype = AA  length = 42
FEATURE                 Location/Qualifiers
REGION                  1..42
                        note = F19N/I32N/A42N
source                  1..42
                        mol_type = protein
                        organism = synthetic construct
SEQUENCE: 3
DAEFRHDSGY EVHHQKLVNF AEDVGSNKGA INGLMVGGVV IN                           42

SEQ ID NO: 4            moltype = AA  length = 42
FEATURE                 Location/Qualifiers
REGION                  1..42
```

```
                    note = F19N/I32N
source              1..42
                    mol_type = protein
                    organism = synthetic construct
SEQUENCE: 4
DAEFRHDSGY EVHHQKLVNF AEDVGSNKGA INGLMVGGVV IA                    42

SEQ ID NO: 5        moltype = AA  length = 42
FEATURE             Location/Qualifiers
REGION              1..42
                    note = F19N/I32N/L34N/A42N
source              1..42
                    mol_type = protein
                    organism = synthetic construct
SEQUENCE: 5
DAEFRHDSGY EVHHQKLVNF AEDVGSNKGA INGNMVGGVV IN                    42

SEQ ID NO: 6        moltype = AA  length = 42
FEATURE             Location/Qualifiers
REGION              1..42
                    note = F19S/I32S/L34S/A42S
source              1..42
                    mol_type = protein
                    organism = synthetic construct
SEQUENCE: 6
DAEFRHDSGY EVHHQKLVSF AEDVGSNKGA ISGSMVGGVV IS                    42

SEQ ID NO: 7        moltype = AA  length = 42
FEATURE             Location/Qualifiers
REGION              1..42
                    note = F19T/I32T/L34T/A42T
source              1..42
                    mol_type = protein
                    organism = synthetic construct
SEQUENCE: 7
DAEFRHDSGY EVHHQKLVTF AEDVGSNKGA ITGTMVGGVV IT                    42

SEQ ID NO: 8        moltype = AA  length = 42
FEATURE             Location/Qualifiers
REGION              1..42
                    note = F19Q/I32Q/L34Q/A42Q
source              1..42
                    mol_type = protein
                    organism = synthetic construct
SEQUENCE: 8
DAEFRHDSGY EVHHQKLVQF AEDVGSNKGA IQGQMVGGVV IQ                    42
```

PROTEIN VARIANT AND COMPOSITION FOR TREATING NEURODEGENERATIVE DISEASE USING THE SAME

BACKGROUND OF THE INVENTION

Field of the Invention

The present invention relates to a novel protein variant and a composition for treating neurodegenerative diseases using the same.

Description of the Related Art

Amyloid beta proteins, which are intrinsically disordered, are arranged in a beta sheet structure through a self-assembly process to form long fibrils having the quaternary structure of proteins. Fibrils formed through the self-assembly process of amyloid beta proteins are major pathological hallmarks of Alzheimer's disease, which is a neurodegenerative disease, and are implicated in the pathogenesis of the disease.

Recently, antibody therapeutics targeting amyloid beta, which is a major marker of Alzheimer's disease, have been introduced in order to overcome the limitations of conventional Alzheimer's disease therapeutics. However, amyloid beta protein itself is a building block of the self-assembly process and may exist in the form of an intermediate and fiber, and fibrosis thereof is also facilitated by other amyloid beta undergoing self-assembly. Accordingly, most of the therapeutic agents that target and remove fibrous amyloid beta do not exhibit the expected effects because amyloid beta proteins are mixed in vivo in various forms.

Accordingly, a method for inhibiting fibrosis of amyloid proteins rather than a method for simply removing amyloid proteins in a specific state may be an alternative. An attempt to correct a Swedish mutation in amyloid precursor proteins, which is known to cause Alzheimer's dementia based on the increase in production of amyloid beta, through gene therapy has recently been reported. In other words, this is a method of conducting gene therapy by removing causative genes using gene scissors.

Although this method is a good attempt to reduce the number of amyloid beta proteins that is increased due to mutation, it has a limitation in that its range of application is restricted because there is a risk of developing Alzheimer's disease even when amyloid beta protein is expressed at a normal level.

Under this background, the present inventors have found that a protein variant in which amino acids at specific positions of amyloid beta protein are substituted with other amino acids inhibits and regulates the formation of amyloid beta fibrils and reduces cytotoxicity when neuroblasts are treated therewith, compared to wild-type amyloid beta. Based thereon, the present invention was completed.

SUMMARY OF THE INVENTION

Therefore, the present invention has been made in view of the above problems, and it is one object of the present invention to provide a protein variant in which amino acids at positions 19 and 32 from the N-terminus of SEQ ID NO: 1 are substituted with other amino acids.

It is another object of the present invention to provide a polynucleotide encoding the protein variant.

It is another object of the present invention to provide a vector including the polynucleotide.

It is another object of the present invention to provide a pharmaceutical composition for preventing or treating a neurodegenerative disease containing the protein variant or the vector.

It is another object of the present invention to provide a method for preventing or treating a neurodegenerative disease including administering the pharmaceutical composition to a subject other than a human.

It is another object of the present invention to provide the use of the protein variant or the vector for prevention or treatment of a neurodegenerative disease.

It is another object of the present invention to provide a health functional food composition for preventing or ameliorating a neurodegenerative disease containing the protein variant or the vector.

It is another object of the present invention to provide a feed composition for preventing or ameliorating a neurodegenerative disease containing the protein variant or the vector.

It is another object of the present invention to provide a composition for controlling fibrosis of amyloid beta containing the protein variant or the vector.

It is another object of the present invention to provide a method for controlling fibrosis of amyloid beta including treating isolated cells with the protein variant or the vector.

In accordance with the present invention, the above and other objects can be accomplished by the provision of a protein variant in which each of amino acids at positions 19 and 32 from the N-terminus of SEQ ID NO: 1 is substituted with another amino acid.

BRIEF DESCRIPTION OF THE DRAWINGS

The above and other objects, features, and other advantages of the present invention will be more clearly understood from the following detailed description taken in conjunction with the accompanying drawings, in which:

FIG. 4 illustrates reduction in cytotoxicity of the variants in which all of phenylalanine 19, isoleucine 32, leucine 34 and alanine 42 are substituted with asparagine.

DETAILED DESCRIPTION OF THE INVENTION

Figure 1:
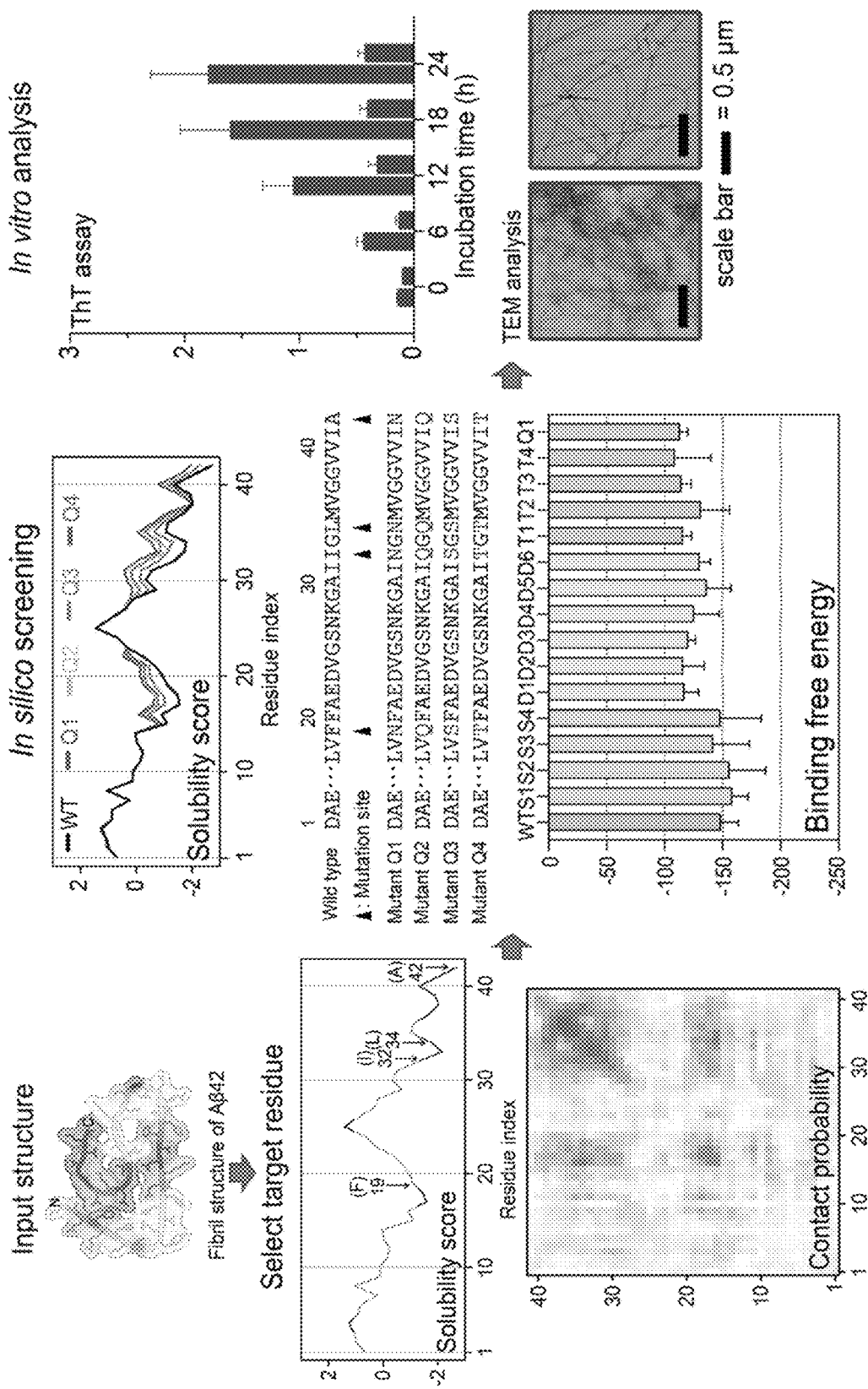
FIG. 1 illustrates a process of selecting a point mutant capable of inhibiting fibrosis based on the structural and kinetic properties of amyloid beta (1-42) (Wild type: SEQ ID NO: 1, Mutant Q1: SEQ ID NO: 5, Mutant Q2: SEQ ID NO: 8, Mutant Q3: SEQ ID NO: 6, and Mutant Q4: SEQ ID NO: 7)

Each description and embodiment disclosed in the present invention may be applied to other descriptions and embodiments. That is, all combinations of various elements disclosed herein fall within the scope of the present invention. In addition, the following detailed description should not be construed as limiting the scope of the present invention.

In addition, those skilled in the art will recognize or appreciate a number of equivalents to the specific embodiments of the present invention disclosed herein through routine experimentation. Also, such equivalents are intended to fall within the scope of the present invention.

It will be further understood that terms, such as "comprise", when used in this specification, specify the presence of stated element, but do not preclude the presence or addition of one or more elements, unless mentioned otherwise.

Hereinafter, the present invention will be described in detail.

The present invention provides a protein variant in which each of amino acids at positions 19 and 32 from the N-terminus of SEQ ID NO: 1 is substituted with another amino acid.

The protein of SEQ ID NO: 1 is an amyloid beta protein, may be designated as a natural or wild-type amyloid beta protein, and may be derived from an amyloid precursor protein, but is not limited thereto.

As used herein, the term "amyloid beta protein" refers to peptides of 36-43 amino acids that are the main component of amyloid plaques found in the brains of patients with Alzheimer's disease, which are dominantly implicated in Alzheimer's disease. Here, amyloid beta protein may be amyloid beta 42.

In the present invention, although the protein of SEQ ID NO: 1 is designated as a representative example of the amyloid beta protein, it is apparent to those skilled in the art that the protein of SEQ ID NO: 1 does not exclude meaningless sequence additions, naturally occurring mutations, or silent mutations thereof before and after the amino acid of SEQ ID NO: 1 and any protein that has equal or corresponding activity to the protein including the amino acid sequence of SEQ ID NO: 1 corresponds to the protein of the present invention.

Specifically, for example, the amyloid beta protein of the present invention may be a protein including the amino acid sequence of SEQ ID NO: 1 or an amino acid sequence having at least 80%, 90%, 95%, or 97% homology or identity thereto. In addition, even a protein having an amino acid sequence, a part of which is deleted, modified, substituted or added also falls within the scope of the protein which is applicable to the mutation of the present invention so long as the amino acid sequence has such homology or identity and exhibits efficacy corresponding to the protein.

That is, it is obvious that the expression "protein or polypeptide having an amino acid sequence set forth in a specific SEQ ID NO: . . . " or "protein or polypeptide including an amino acid sequence set forth in a specific SEQ ID NO: . . . " is intended to mean that even a protein having an amino acid sequence, a part of which is deleted, modified, substituted or added may also be used in the present invention so long as it has equal or corresponding activity to the polypeptide including the amino acid sequence of the corresponding SEQ ID NO. For example, it is obvious that "polypeptide including an amino acid sequence of SEQ ID NO: 1" may fall within the scope of "polypeptide including an amino acid sequence of SEQ ID NO: 1" so long as it has equal or corresponding activity thereto.

As used herein, the term "variant" refers to a protein that has one or more amino acids different from the recited sequence in conservative substitution and/or modification, but maintains functions or properties thereof. Such a variant is generally identified by modifying one or more amino acids in the amino acid sequence of the protein and then evaluating the properties of the modified protein. That is, the ability of the variant may be increased, maintained, or decreased compared to the wild-type protein. In addition, some variants may include variants in which one or more portions such as N-terminal leader sequences or transmembrane domains have been removed. Other variants may include variants in which a portion is removed from the N- and/or C-terminus of the mature protein. The term "variant" may be used interchangeably with terms such as "modification", "modified protein", "modified polypeptide", "mutant", "mutein", and "divergent". Any term may be used without particular limitation so long as it includes the concept of "variation".

As used herein, the term "conservative substitution" refers to substitution of at least one amino acid with another amino acid having similar structural and/or chemical properties. The variant may have, for example, one or more conservative substitutions while retaining one or more biological activities. Such amino acid substitution may generally occur based on similarity in the polarity, charge, solubility, hydrophobicity, hydrophilicity and/or amphipathic nature of the residues. For example, among amino acids having electrically charged amino acids, positively charged (basic) amino acids include arginine, lysine, and histidine, negatively charged (acidic) amino acids include glutamic acid and aspartic acid, and among amino acids having an uncharged amino acid, nonpolar amino acids include glycine, alanine, valine, leucine, isoleucine, methionine, phenylalanine, tryptophan, and proline, and polar or hydrophilic amino acids include serine, threonine, cysteine, tyrosine, asparagine, and glutamine, and aromatic amino acids include phenylalanine, tryptophan and tyrosine.

In addition, variants may include deletions or additions of amino acids that have minimal effects on the secondary structure and properties of the polypeptide. For example, the polypeptide may be conjugated with a signal (or leader) sequence at the N-terminus of the protein that is implicated in the co-translational or post-translational transfer of the protein. The polypeptide may also be conjugated with other sequences or linkers to identify, purify, or synthesize the polypeptide.

The protein variant may have inhibited amyloid beta fibrosis compared to a wild-type protein.

As used herein, the term "inhibition of amyloid beta fibrosis" refers to inhibition of aggregation of amyloid beta, and may be used interchangeably with "fibrosis inhibition," "aggregation inhibition," "fibrosis control," or "aggregation control".

There is no limitation as to the substitution with another amino acid as long as an amino acid different from the amino acid before substitution is used. Specifically, there is no limitation as to the substitution with another amino acid as long as the amino acids at positions 19 and 32 from the N-terminus of the amino acid sequence of SEQ ID NO: 1 are substituted with other amino acid residues.

In addition, the protein variant may be characterized in that at least one of amino acids at positions 34 and 42 is substituted with another amino acid.

Meanwhile, it is obvious that the expression "a specific amino acid is substituted" as used herein means that the amino acid is substituted with an amino acid different from the amino acid before substitution, even if it is not specifically described that it is substituted with another amino acid.

The protein variant may be one in which at least one of amino acids 19 and 32 in the amino acid sequence of SEQ ID NO: 1 is substituted with a polar and uncharged amino acid, specifically asparagine (N), glutamine (Q), serine (S) or threonine (T), and more specifically, asparagine (N).

The protein variant of the present invention in which amino acids 19 and 32 from the N-terminus of SEQ ID NO: 1 are substituted with other amino acids may also include protein variants substituted with amino acids other than the amino acids at positions 19 and 32. Specifically, at least one of amino acids at positions 34 and 42 may be substituted with at least one other amino acid, that is, asparagine (N), glutamine (Q), serine (S) or threonine (T), and may further include substitution of an amino acid at a certain position with another amino acid.

The two amino acids may be phenylalanine (Phe, F) at the $19^{th}$ position from the N-terminus of SEQ ID NO: 1 and isoleucine (Ile, I) at the $32^{nd}$ position therefrom. Also, it is obvious that a protein having an amino acid sequence, a part of which is deleted, modified, substituted or added also falls within the scope of the protein so long as the amino acid sequence exhibits efficacy corresponding to the protein variant.

Specifically, the protein variant of the present invention may have an amino acid sequence selected from the group consisting of amino acid sequences set forth in SEQ ID NOS: 2 to 8, specifically, may have an amino acid sequence selected from the group consisting of amino acid sequences set forth in SEQ ID NOS: 2 to 5, more specifically, may have an amino acid sequence selected from the group consisting of amino acid sequences set forth in SEQ ID NOS: 2 to 4. In addition, the protein variant of the present invention may include a polypeptide having at least 80%, 90%, 95%, 96%, 97%, 98%, or 99% homology or identity to the amino acid sequence. In addition, it is obvious that a protein having an amino acid sequence, a part of which is deleted, modified, substituted or added also falls within the scope of the protein so long as the amino acid sequence exhibits efficacy corresponding to the protein variant.

As used herein, the term "homology" or "identity" refers to a degree to which two given amino acid sequences or base sequences are related to each other and may be expressed as a percentage. The terms "homology" and "identity" may often be used interchangeably.

Sequence homology or identity of a conserved polynucleotide or polypeptide is determined by standard alignment algorithms and default gap penalties established by the program that may be used in combination therewith. A substantially homologous or identical sequence is generally hybridized with at least about 50%, 60%, 70%, 80% or 90% of the entire or full-length sequence under moderate or highly stringent conditions. Hybridization is also performed in consideration of polynucleotides containing degenerate codons instead of codons in the polynucleotides.

Whether or not two polynucleotide or polypeptide sequences have homology, similarity or identity to each other may be determined, for example, using a known computer algorithm such as the "FASTA" program using a default parameter disclosed in Pearson et al (1988) [Proc. Natl. Acad. Sci. USA 85]: 2444. Alternatively, they may be determined using the Needleman-Wunsch algorithm (Needleman and Wunsch, 1970, J. Mol. Biol. 48: 443-453) as performed in the NeedleMann program of the EMBOSS package (The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215)]: 403 (1990); Guide to Huge Computers, Martin J. Bishop, [ED.,] Academic Press, San Diego, 1994, and [CARILLO ETA/.] (1988) SIAM J Applied Math 48: 1073.). For example, the homology, similarity or identity may be determined using BLAST or ClustalW of the National Center for Biotechnology Information.

The homology, similarity or identity of polynucleotides or polypeptides may be determined by comparing sequence information using a GAP computer program (e.g., Needleman et al. (1970), J Mol Biol 48: 443) as disclosed in Smith and Waterman, Adv. Appl. Math (1981) 2:482. Briefly, the GAP program defines the homology, similarity or identity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) Nucl. Acids Res. 14: 6745, as disclosed in Schwartz and Dayhoff, eds., Atlas Of Protein Sequence And Structure, National Biomedical Research Foundation, pp. 353 to 358 (1979); (2) a penalty of 3.0 for each gap and an additional penalty of 0.10 for each symbol in each gap (or gap open penalty of 10, gap extension penalty of 0.5); and (3) no penalty for end gaps.

In addition, whether or not two polynucleotide or polypeptide sequences have homology, similarity or identity to each other may be determined by comparing the sequences using Southern hybridization experiments under defined stringent conditions, and the appropriate defined hybridization conditions fall within the technical scope and may be determined by methods well known to those skilled in the art (for example, J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York).

In one embodiment of the present invention, based on the structure in order to inhibit fibrosis of amyloid beta protein, a protein variant was produced by substituting amino acids at positions 19 and 32 of amyloid beta protein with another amino acid, such as asparagine, which reduces hydrophobicity, and further substituting at least one of amino acids at the positions 34 and 42 thereof with another amino acid. Whether or not amyloid beta fibrosis can be controlled using the protein variant was determined. The result showed that the protein variant reduces the fibril formation rate, which is a characteristic of wild-type amyloid beta, and also reduces the cytotoxicity that occurs during amyloid fibrosis. In addition, it was found that, unlike the conventional methods for inhibiting amyloid fibrosis, the formation rate and length of amyloid fibrils can be controlled through point mutants of amyloid beta proteins, rather than external additives such as antibodies and nanoparticles.

The present invention also provides a polynucleotide encoding the protein variant and a vector including the polynucleotide.

As used herein, the term "polynucleotide" refers to a polymer of nucleotides in which nucleotide units are linked in a long chain form through covalent bonds, generally refers to a DNA or RNA strand having a certain length or longer, and means a fragment of a polynucleotide encoding the protein variant in the present invention.

As used herein, the term "vector" refers to any medium used for cloning and/or transfer of a base to a host cell. A vector may be a replicon that is capable of causing replication of a DNA fragment bound thereto. The term "replicon" refers to any genetic unit (e.g., plasmid, phage, cosmid, chromosome or virus) that functions as a self-unit of DNA replication in vivo, i.e. is capable of replicating by its own regulation. The term "vector" includes viral and non-viral media for introducing a base into a host cell in vitro, ex vivo or in vivo, and may also include minispherical DNA. For example, the vector may be a plasmid that does not have a bacterial DNA sequence. Removal of enriched bacterial DNA sequences in the CpG region has been done to reduce transgene expression silencing and to cause more sustained expression from plasmid DNA vectors (e.g., Ehrhardt, A. et al. (2003) HumGene Ther 10: 215-25; Yet, N. S. (2002) MoI Ther 5: 731-38; Chen, Z. Y. et al. (2004) Gene Ther 11: 856-64). In addition, the vector may include a transposon (Annu Rev Genet. 2003; 37:3-29.), or an artificial chromosome. Preferably, the vector may be a pACYC177, pACYC184, pCL1920, pECCG117, pUC19, pBR322 or pMW118 vector, but is not limited thereto.

The present invention also provides a pharmaceutical composition for preventing or treating a neurodegenerative disease containing the protein variant or the vector.

As used herein, the terms "protein variant" and "vector" are as defined above.

As used herein, the term "neurodegenerative disease" includes, in a broad sense, all conditions characterized by degeneration in nerve cells, but generally does not include factors other than the nervous system cells such as cerebrovascular disorders, trauma, and metabolic abnormalities. Specifically, the neurodegenerative disease may include dementia, Alzheimer's disease, Parkinson's disease and is, more specifically, Alzheimer's disease, but is not limited thereto.

Alzheimer's disease is the most common neurodegenerative brain disease causing dementia and is characterized by slow onset and gradual deterioration in cognitive function. It shows symptoms of cognitive impairment such as memory loss, deterioration in language ability, deterioration in temporal and spatial understanding ability, deterioration in judgment and daily living performance, gait disturbance, and movement disturbance.

As used herein, the term "prevention" refers to any action that suppresses or delays the onset of neurodegenerative diseases by administration of the protein variant or the vector.

As used herein, the term "treatment" means any action that can ameliorate or beneficially alter the symptoms of neurodegenerative diseases by administration of the protein variant or the vector.

The pharmaceutical composition of the present invention may contain 0.01 to 80%, specifically 0.01 to 70%, more specifically 0.01 to 60% by weight of the protein variant or vector based on the total weight of the composition, but the content of the pharmaceutical composition is not limited thereto so long as the preventive or therapeutic effects for neurodegenerative diseases can be obtained.

In addition, the pharmaceutical composition may further contain a pharmaceutically acceptable carrier, excipient or diluent commonly used in the preparation of the pharmaceutical composition, and the carrier may include a non-naturally occurring carrier. Specific examples of the carrier, excipient and diluent include, but are not limited to, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate or mineral oil.

In addition, the pharmaceutical composition may have a formulation selected from the group consisting of tablets, pills, powders, granules, capsules, suspensions, oral liquids and solutions, emulsions, syrups, sterilized aqueous solutions, non-aqueous solvents, suspensions, emulsions, lyophilizates and suppositories in accordance with a conventional method and may be any one of various oral or parenteral formulations. In the case of formulation, the pharmaceutical composition may be prepared using a diluent or excipient such as a commonly used filler, extender, binder, wetting agent, disintegrant or surfactant. Solid formulations for oral administration may include tablets, pills, powders, granules, capsules and the like, and may be prepared by mixing at least one excipient, for example, starch, calcium carbonate, sucrose, lactose, gelatin or the like. In addition to simple excipients, lubricants such as magnesium stearate and talc are also used. Liquid formulations for oral administration may be suspensions, oral liquids and solutions, emulsions, syrups and the like, and may contain various excipients such as wetting agents, sweeteners, fragrances, preservatives and the like, in addition to water and liquid paraffin, which are simple diluents that are commonly used. Formulations for parenteral administration may include sterilized aqueous solutions, non-aqueous solutions, suspensions, emulsions, lyophilizates and suppositories. Examples of non-aqueous solvents and suspensions include propylene glycol, polyethylene glycol, vegetable oil such as olive oil, injectable esters such as ethyl oleate, and the like. Examples of the suppository base include, but are not limited to, Witepsol, macrogol, Tween 61, cacao butter, laurin butter, glycerogelatin and the like. The present invention also provides a method for preventing or treating a neurodegenerative disease including administering the pharmaceutical composition to a subject other than a human.

As used herein, the terms "protein variant", "vector", "neurodegenerative disease", "prevention" and "treatment" are as defined above.

As used herein, the term "administration" refers to introduction of the pharmaceutical composition to a subject using an appropriate method.

As used herein, the term "subject" refers to any of animals, such as rats, mice and livestock, including humans, that have or may develop a neurodegenerative disease. Specifically, the subject is, for example, a mammal including a human.

The pharmaceutical composition of the present invention may be administered in a pharmaceutically effective amount.

The term "pharmaceutically effective amount" refers to an amount which is sufficient for treating a disease at a reasonable benefit/risk ratio applicable to all medical treatments, and the effective dosage level may vary depending on a variety of factors including severity of the disease, activity of the drug, the age, body weight, state of health and gender of the patient, sensitivity of the patient to the drug, administration time, administration route and excretion rate of the composition according to the present invention, treatment period, drugs used in combination therewith, and other factors well-known in the field of pharmaceuticals.

The pharmaceutical composition may be administered as a single therapeutic agent or in combination with other therapeutic agents and may be administered sequentially or simultaneously with conventional therapeutic agents. In addition, single or multiple administration is possible. Taking into consideration these factors, it is important to administer the minimum amount sufficient to achieve maximum efficacy without side effects. This may be easily determined by those skilled in the art.

In addition, the pharmaceutical composition may be orally or parenterally administered (e.g., intravenously subcutaneously, intraperitoneally or topically applied) in accordance with the desired method and the dosage may vary depending on the patient's condition and weight, the degree of disease, drug form, administration route and time, but may be appropriately selected by those skilled in the art. For example, the pharmaceutical composition may be administered in a single dose or divided into multiple doses over 4 weeks in an amount of about 0.001 to 1,000 mg/kg, more specifically 0.05 to 200 mg/kg, most specifically, 0.1 to 100 mg/kg. A preferred dosage may be appropriately selected by those skilled in the art in accordance with the condition and weight of the subject, the degree of disease, the drug form, and the route and period of administration.

The present invention also provides a health functional food composition for preventing or ameliorating a neurodegenerative disease containing the protein variant or the vector.

The present invention also provides a feed composition for preventing or ameliorating a neurodegenerative disease containing the protein variant or the vector.

As used herein, the terms "protein variant", "vector", "neurodegenerative disease", and "prevention" are as defined above.

As used herein, the term "amelioration" refers to any action that at least reduces parameters, for example, the severity of symptoms, related to the condition that is treated by administration of the protein or the vector.

As used herein, the term "health functional food" refers to a food produced and processed using raw materials or ingredients having useful functions for the human body pursuant to the Health Functional Food Act No. 6727, and the term "functional" refers to a beneficial effect for health such as regulation of nutrients appropriate for structures and functions of the human body or physiological effects. Meanwhile, the term "health food" refers to food that has an activity of maintaining or improving health compared to general food, and the term "health supplement" refers to food to supplement health. In some cases, the terms "health functional food", "health food" and "health supplement" may be used interchangeably.

The novel protein variant or the polynucleotide encoding the same may be used alone or in combination with other food or food additives and may be suitably used in accordance with a conventional method.

The health functional food composition of the present invention may be prepared in accordance with a method commonly used in the art. The health functional food composition may be prepared by adding raw materials and ingredients commonly added in the art. Specifically, the health functional food composition may further contain a physiologically acceptable carrier, the type of carrier is not particularly limited and any carrier commonly used in the art may be used.

In addition, the health functional food composition may contain a food additive such as a preservative, a disinfectant, an antioxidant, a colorant, a color fixative, a bleaching agent, a seasoning, a sweetener, a flavoring, an expander, an enhancer, an emulsifier, a thickener, a coating agent, a gum base, an anti-foaming agent, a solvent, an improving agent, or the like. The additive may be selected depending on the type of food and used in an appropriate amount.

In addition, any formulation may be used for the health functional food without limitation as long as it is cytologically acceptable. The composition for health functional food of the present invention may be prepared in various types of formulations and the food of the present invention has advantages of avoiding side effects that may occur during long-term administration of the drug since it contains food as a raw material and of having excellent portability, unlike general drugs. Therefore, the food may be ingested as an adjuvant for enhancing the effect of preventing or ameliorating neurodegenerative diseases.

The novel protein variant of the present invention or the vector including the polynucleotide encoding the same may be present in any of various wt % in the health functional food composition so long as it can exhibit the effect of preventing or ameliorating neurodegenerative diseases. Specifically, the protein variant or the vector may be present in an amount of 0.00001 to 100% by weight or 0.01 to 80% by weight based on the total weight of the health functional food composition, but is not limited thereto. In the case of long-term intake for the purpose of health and hygiene or for the purpose of health management, the amount may be within the range defined above and the active ingredient may be used in an amount exceeding the above range because there is no problem in terms of safety.

As used herein, the term "feed" means any natural or artificial diet, meal, or the like, or an ingredient of the meal, intended for or suitable for being eaten, ingested, and digested by an animal.

The type of feed is not particularly limited and feeds commonly used in the art may be used. Non-limiting examples of the feed include plant feeds such as grains, roots, food processing by-products, algae, fibrils, pharmaceutical by-products, oils and fats, starches, gourds or grain by-products, and animal feeds such as proteins, inorganic materials, oils and fats, minerals, single-cell proteins, zooplankton or food. These may be used alone or in combination of two or more thereof.

The feed composition of the present invention may be prepared in any of various forms known in the art. In addition, the composition may further contain substances exhibiting various effects such as effects of replenishing nutrients, preventing weight loss, improving digestion of fibers in feed, improving oil quality, preventing reproductive disorders, improving fertility rate, and preventing of stress to high temperatures in summer, for example, minerals such as sodium bicarbonate, bentonite, magnesium oxide, and complex minerals, trace minerals such as zinc, copper, cobalt, and selenium, vitamins such as carotene, vitamin E, vitamins A, D, and E, nicotinic acid, and vitamin B complexes, protective amino acids such as methionine and lysine, protective fatty acids such as calcium fatty acid, bacterium and yeasts such as probiotics (lactic acid bacteria), yeast cultures, and mold fermented products.

The present invention also provides a composition for controlling fibrosis of amyloid beta containing the protein variant or the vector.

The present invention also provides a method for controlling fibrosis of amyloid beta including treating isolated cells with the protein variant or the vector.

As used herein, the terms "protein variant", "vector", "amyloid beta", and "fibrosis" are as defined above.

In a specific embodiment of the present invention, it was found that the protein variant of the present invention based on the structure of amyloid beta (1-42) causing amyloid fibrosis reduces the fiber formation rate, which is a characteristic of wild-type amyloid beta and reduces cytotoxicity during amyloid fibrosis. In addition, unlike conventional methods for inhibiting amyloid fibrosis, the formation rate and length of amyloid fibrils are controlled by point mutants of amyloid beta protein, rather than external additives such as antibodies and nanoparticles.

Hereinafter, the present invention will be described in more detail with reference to the following examples. These examples are provided only for better understanding of the present invention and should not be construed as limiting the scope of the present invention.

EXPERIMENTAL EXAMPLE

Experimental Example 1: Selection of Protein Variants Based on Computational Calculation and Structure In order to determine the effects of point mutations on the solubility of proteins, the solubility scores before and after substitution at a neutral pH were calculated using the CamSol web server (http://www-vendruscolo.ch.cam.ac.uk/camsolmethod.html).

GROMACS 2020.4 and GROMACS 4.5.5 were used for molecular dynamics computational simulation. In addition, CHARMM36m forcefield (Huang, J.; Rauscher, S.; Nawrocki, G.; Ran, T.; Reig, M.; de Groot, B. L.; Grubmuller, H.; MacKerell, A. D. Nature Methods 2017, 14 (1), 71-73.) was used for simulations.

The initial structure of the amyloid beta protein was identified using the published PDB structure (PDB code: 5OQV). A replica exchange molecular dynamics computational simulation was performed at a temperature between 400K and 500K for enhanced structural sampling. A total of 10,000 structures were obtained from 5 replicas by 20 ns calculation and then 50 structures that are highly likely to be present in a solution in association with the results of solution-phase X-ray small angle scattering using an ensemble optimization method (EOM) were selected.

The dynamics of the dimer were computer-simulated by replicating the structure in duplicate based on the extended structure having the radius of gyration among the 50 selected structures. The calculation of 400 ns was performed on a total of 48 replicas, a total of 19.2 μs was calculated, and the structure of the dimer that reached the equilibrium state was observed.

A TIP3P cubic water box was produced at a pH of 7 and sodium and chlorine ions were added thereto at a concentration of 20 mM. Calculation was performed at 2 fs intervals using the SHAKE algorithm of the GROMACS 2020.4 program. Electrostatic interactions were calculated using the particle mesh Ewald (PME) method with a cutoff of 1.2 nm and a cutoff of 1.2 nm was used for van der Waals interactions. In this case, a velocity-rescaling thermostat was used. In addition, REMD was performed with an exchange at a temperature between 300K and 400K in 48 replicas. At this time, the exchange was performed every 2 ps and the average exchange probability was 0.3.

Experimental Example 2: Materials

All experimental materials not mentioned herein were obtained from commercially available products.

The synthesized wild-type and point mutant (purity of 95% or more) amyloid beta 42 were purchased from Anygen (Gwangju, Republic of Korea). The protein concentration was determined using a UV-visible (UV-Vis) spectrophotometer (E280 nm=1490 $M^{-1}$ $cm^{-1}$). A tris(hydroxymethyl)aminomethane-hydrogen chloride standard solution (1M, pH 7.4) was purchased from Biosesang (Daejeon, Republic of Korea). The solvent used herein was HPLC-grade water (JT Baker, Phillipsburg, NJ, USA).

Experimental Example 3: Cell Culture

SH-SY-5Y neuroblastoma cells were purchased from the Korean Cell Line Bank (Seoul, South Korea) and incubated in a 1:1 mixture of Dulbecco's modified eagle medium/F-12 nutrient mixture ham (DMEM/F-12; WelGENE) supplemented with 10% fetal bovine serum (FBS; Capricorn Scientific GmbH, Ebsdorfergrund, Germany) and 1% antibiotic (10,000 U/mL penicillin G, 10,000 μg/mL streptomycin and 25 μg/mL amphotericin B; Hyclone, Logan, UT, USA). The antibiotic was sterilized through a 0.2 μm filter before use and the cells were incubated at 37° C. under humid conditions including 5% $CO_2$.

Experimental Example 4: Amyloid Beta Fibrosis Experiment

A ThT fluorescence assay was performed in order to determine the fibrosis rate of wild-type amyloid beta and protein variant thereof.

Specifically, fibrosis of 10 uM of each sample was induced at 37° C. in the presence of a 20 uM tris(hydroxymethyl)aminomethane-hydrogen chloride solution (pH 7.4) along with 5 uM ThT.

Specifically, the sample was seeded on a Corning 96-well black polystyrene microplate (Corning 3603, Corning, New York, N.Y., USA) and was then sealed with an EASYseal™ sealing film (Greiner-Bio-One). Then, the fluorescence intensity was measured with a Synergy H1 microplate reader (BioTek, Winooski, VT, USA). At this time, the excitation wavelength and the emission wavelength were 446 nm and 482 nm, respectively.

Experimental Example 5: Morphological Analysis of Fibrils Using Transmission Electron Microscopy (TEM)

Negative staining was performed using uranyl acetate to order to visualize the fibrosis of amyloid beta protein.

Specifically, a 0.5% w/v uranyl acetate stock solution was prepared from HPLC grade water and filtered through a 0.22 μm disposable syringe filter. A total of 10 μM Aβ peptide was incubated for 24 hours and was transferred to a 400-mesh formvar/carbon Cu(II) grid (Electron Microscopy Science, Hatfield, PA, USA). The incubated fibril sample (5 μL) was spotted on a Cu(II) grid at 20° C. for 3 minutes. The grid was washed twice immediately after the sample was removed therefrom using a 0.5% w/v uranyl acetate solution and each sample was stained with 5 μL of a uranyl acetate solution for 1 minute. Then, the staining solution was removed and then the sample was dried at 20° C. for 4 hours.

In order to measure the fiber length of amyloid beta protein, images were analyzed using Able Image Analyzer v3.6. Here, the fiber length was defined by measuring the distance from the end of the fiber, which is detectable, to the opposite end thereof.

TEM images were observed with a JEM-F200 (TFEG) (JEOL Ltd, Japan) field-emission transmission electron microscope (National Center for Inter-University Research Facilities (NCIRF), Seoul National University, Seoul, Republic of Korea).

Experimental Example 6: Cell Viability Test Cell Viability was Evaluated by MTT Assay Specifically, 15,000 cells were grown in each well of a 96-well plate and incubated for 24 hours. SH-SY-5Y cells were treated with amyloid beta monomers and fibrils thereof and then cultured for 2 days. Then, the MTT solution was added to the medium and incubated at 37° C. for 3 hours to form the MTT-formazan product. The amount of the product was quantified as the extent of absorption at a wavelength of 540 nm.

Each test was conducted on three samples at a time and the entire test was repeated three times to ensure reproducibility.

EXAMPLE

Example 1: Selection of Point Mutants Capable of Inhibiting Fibrosis Based on Structural and Kinetic Properties of Amyloid Beta (1-42)

The region where hydrophobic interactions predominantly occur for efficient inhibition of fibrosis was found since the hydrophobic interaction between amyloid beta (1-42) chains plays an important role in the fibrosis stage of amyloid beta (1-42).

For this purpose, the calculation was performed in consideration of the characteristics of the wild-type amyloid beta (1-42) fiber structure. As a result, the solubility score of each amino acid could be obtained. As can be seen from FIG. 1 based on these results, the region from leucine 17 to phenylalanine 19 and the region from isoleucine 32 to alanine 42 were identified as two regions having a particularly low solubility score, that is, a solubility score of lower than −1 (FIG. 1).

Another process essential for fibrosis is initial interaction. Therefore, as the subsequent step, calculation was performed for a sufficiently long time using molecular dynamics computational simulation, which ascertained that the two amyloid beta (1-42) chains that reached equilibrium interact with each other.

As a result, as can be seen from FIG. 1, two regions identified based on the solubility score of the previous amino acid through intra-chain and inter-chain contact probability maps contact each other with a higher probability compared to the other regions (FIG. 1). In this way, it is considered that the two (that is, primary and secondary) computational simulation methods show a correlation with each other and yield the same result because the hydrophobic interaction plays a key role in the initial amyloid fibrosis stage.

Then, four hydrophobic amino acids, namely, phenylalanine 19, isoleucine 32, leucine 34, and alanine 42, were selected as targets for point mutation in the two regions identified through the computational simulation method. In addition, the four selected protein variants were substituted with asparagine, glutamine, serine and/or threonine, which are four polar and uncharged amino acids, respectively, and the solubility scores of the four protein variants were calculated. As a result, as can be seen from FIG. 1, substitution with asparagine among the four amino acids increased the solubility score the most and substitution with other amino acids also increased the solubility score. In addition, binding free energy calculation results using the molecular dynamics computational simulation method showed that protein variants substituted with at least two amino acids are required to efficiently interfere with fibrosis (FIG. 1).

Example 2: Determination of Amyloid Fibril Shape and Length Changes During Fibrosis of Amyloid Beta (1-42) in Native- (Wild-Type) Protein and Protein Variant of Present Invention Fibrosis was induced in 10 uM of each of the native (wild-type) amyloid beta (1-42) and the protein variant prepared in the present invention at 37° C. for 1 day. Then, a fiber-forming solution was transferred to a copper grid plate on which a foam bar was deposited and then negative staining was performed using uranyl acetate (FIG. 2D).

Figure 2A:
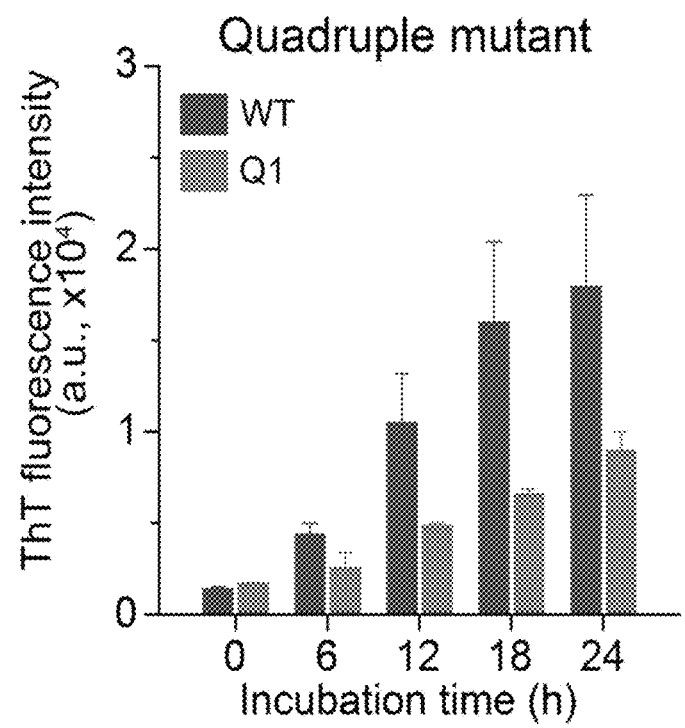
FIGS. 2A to 2E illustrate changes in the amyloid fiber shape and length of each of the wild-type protein and the protein variant of the present invention during fibrosis of amyloid beta (1-42)
Figure 2B:
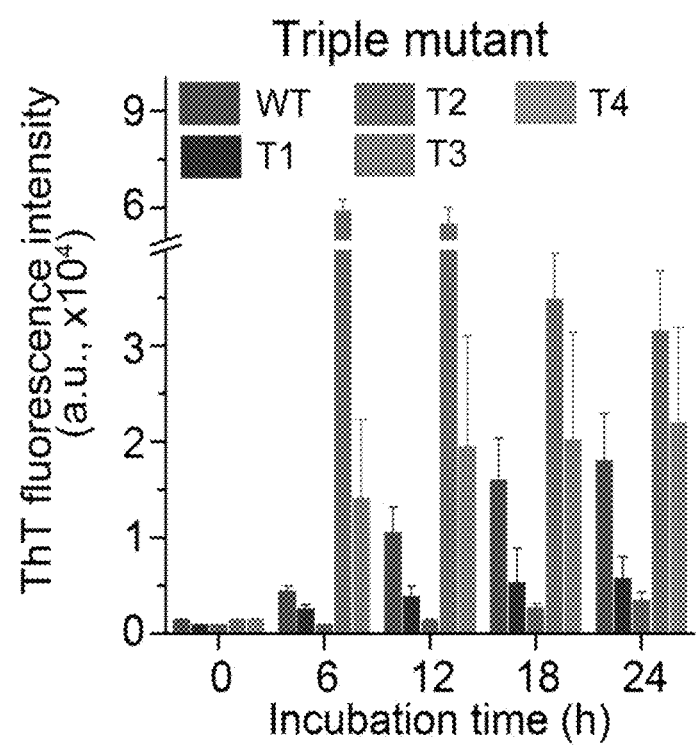
Figure 2C:
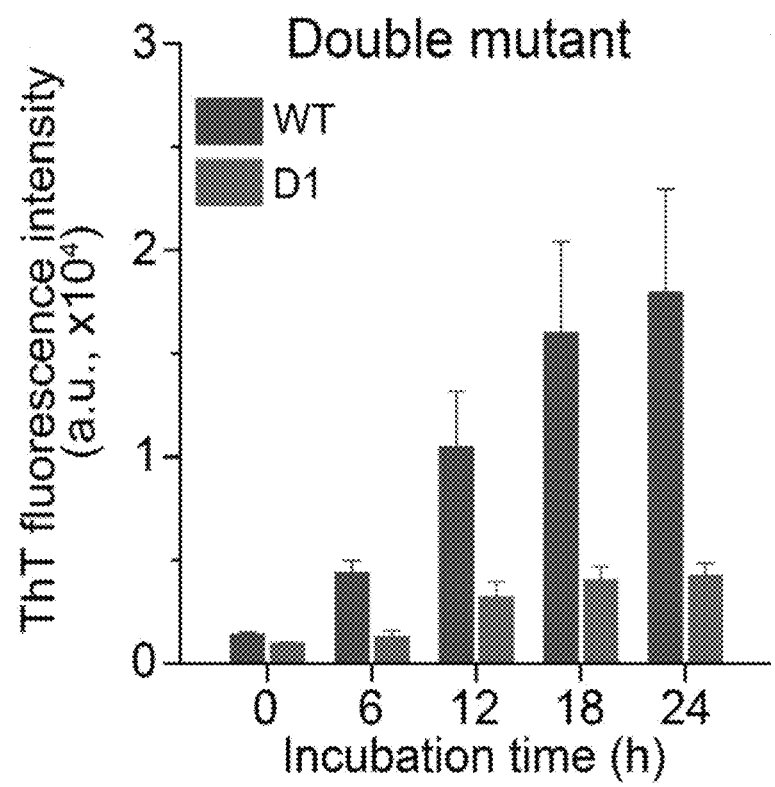
Figure 2D:
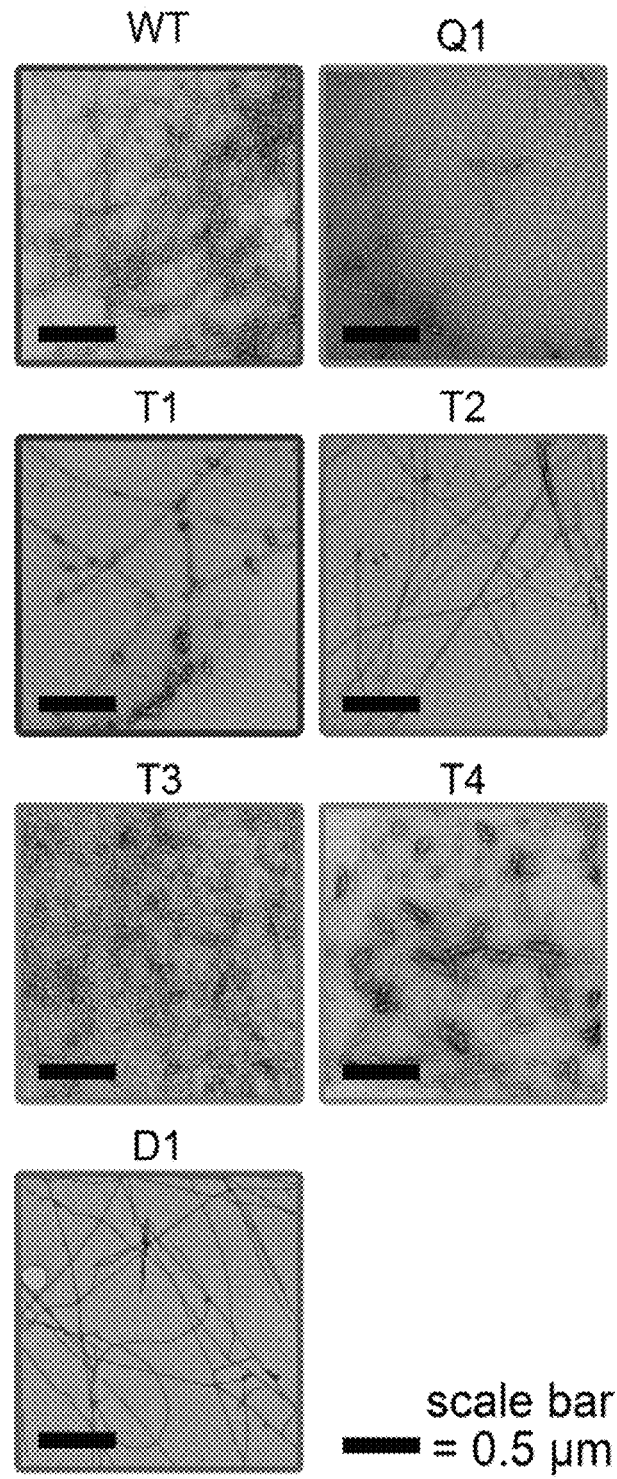
Figure 2E:
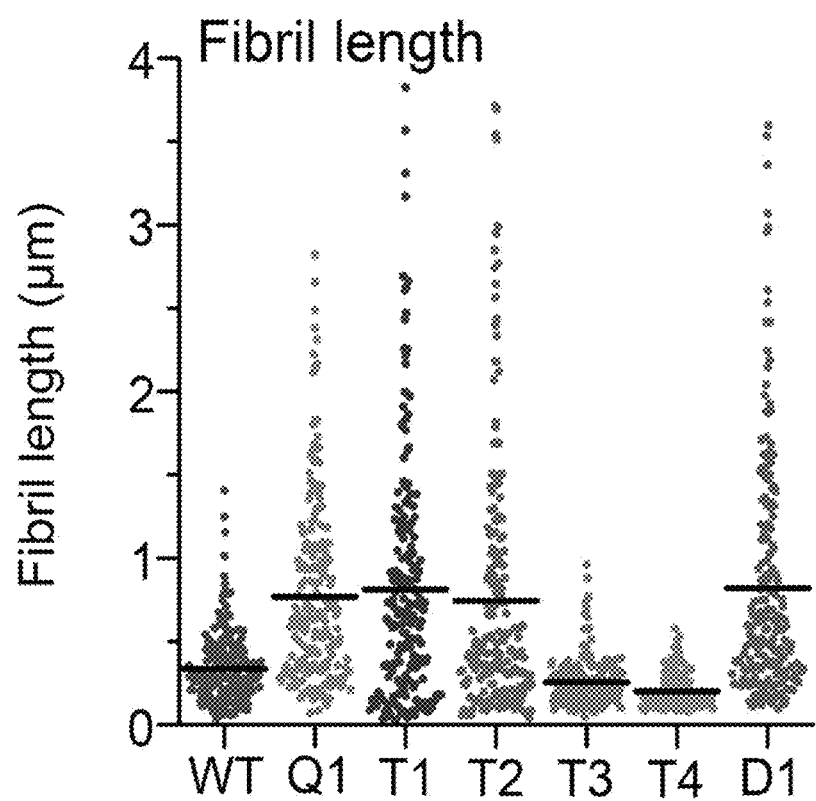
Figure 3A:
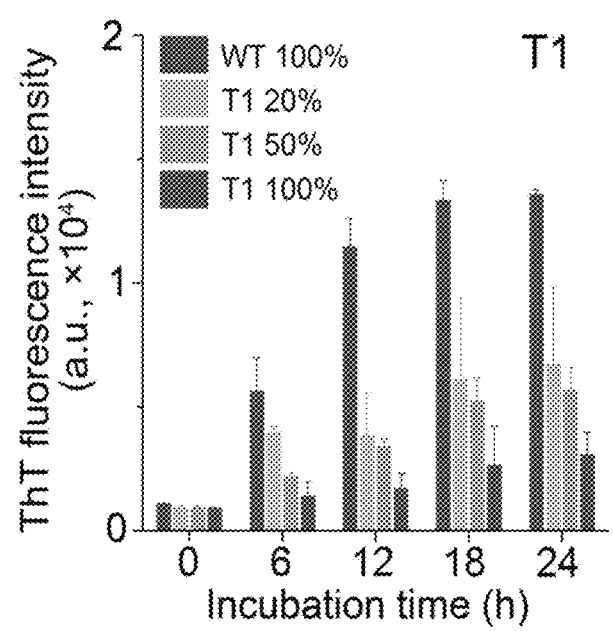
FIGS. 3A to 3G illustrate changes in the shape, length and cytotoxicity of fibrils depending on the ratio of the protein variant during the fibrosis of amyloid beta (1-42) when the wild-type protein and the protein variant of the present invention that succeeded in inhibiting fiber formation are mixed.
Figure 3B:
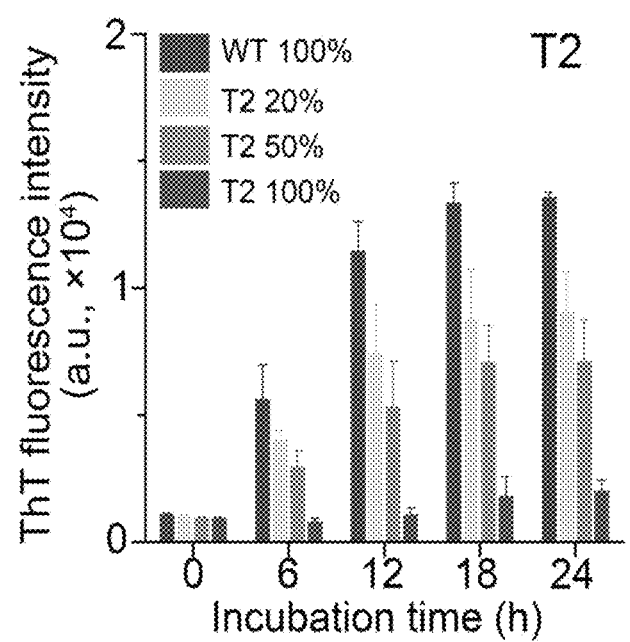
Figure 3C:
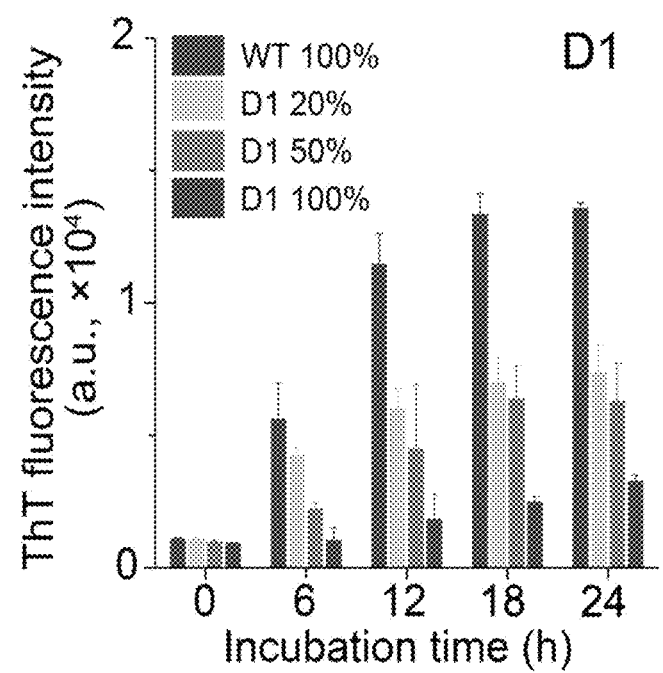
Figure 3D:
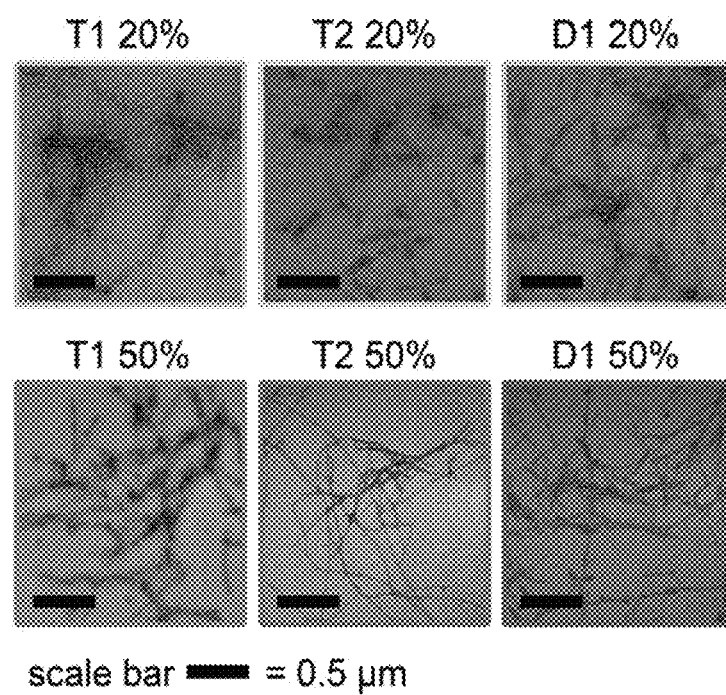
Figure 3E:
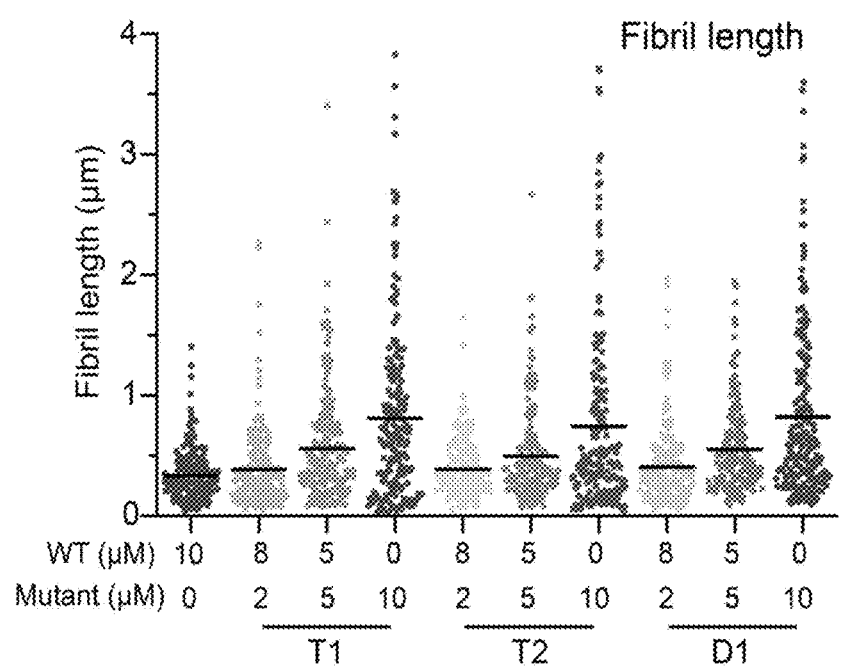
Figure 3F:
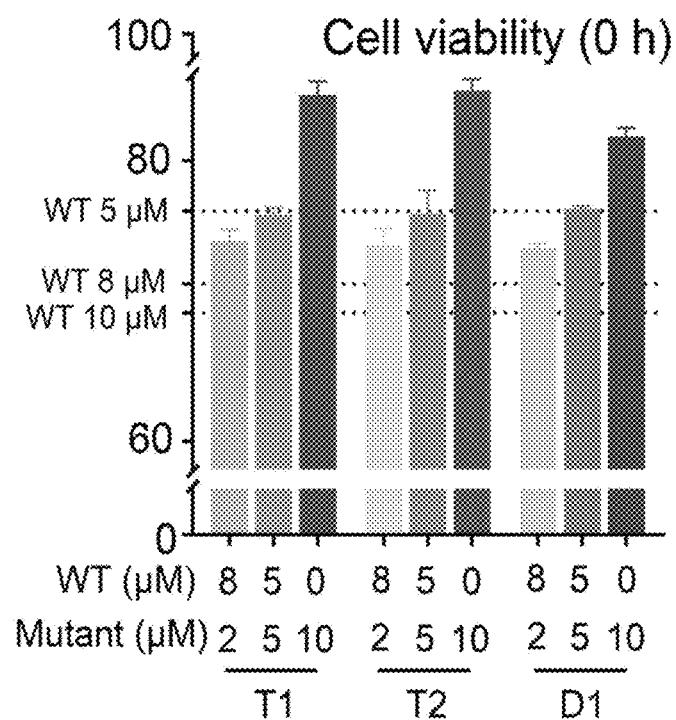
Figure 3G:
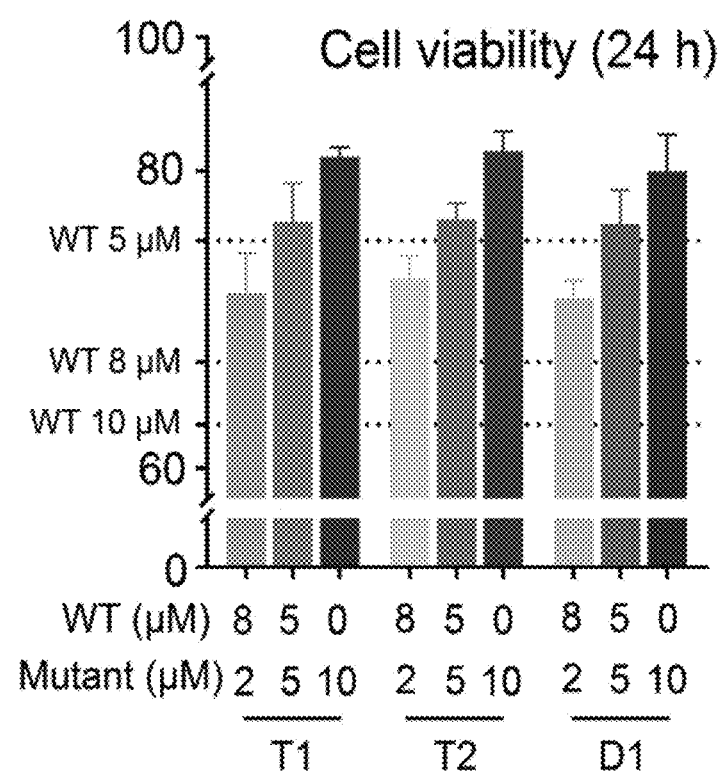

When 205 rotations per minute were applied to a test tube under the experimental conditions, the average length of wild-type amyloid beta fibrils was 334.5 nanometers (nm) and the standard deviation was 218.2 nm (FIG. 2E).

Then, the average length of the fibrils of the protein variant in which four hydrophobic amino acids selected through computational simulation were substituted with asparagine under the same experimental conditions as in Example 1 was 766.0 nm, and the standard deviation was 551.1 nm, which were greatly increased compared to wild-type amyloid beta (FIG. 2E).

Interestingly, the protein variant in which three hydrophobic amino acids were substituted with asparagine had a slight increase in the average fiber length, whereas the protein variant substituted with phenylalanine 19, leucine 34, and alanine 42, and the protein variant substituted with isoleucine 32, leucine 34, and alanine 42 had average fiber lengths of 254.4 nm and 199.3 nm, respectively, which were decreased compared to the average length of the wild-type amyloid beta fibrils.

In particular, it was found that the protein variant in which only phenylalanine 19 and isoleucine 32, which were common in two protein variants having an increased average fiber length, were substituted with asparagine also maintained the fibrosis rate characteristics engineered to an average fiber length of 819.4 nm.

In addition, the average length of the formed fibrils increased and the rate of fiber formation was measured based on fluorescence intensity using Thioflavin T. The result showed that the mutant designed using computational simulation could kinetically inhibit fibrosis of amyloid beta protein (FIGS. 2A to 2C).

In addition, the protein variant in which both phenylalanine 19 and isoleucine 32 were substituted, and leucine 34 and alanine 42 were further substituted with asparagine also reduced cytotoxicity and inhibited fibrosis (FIGS. 2A and 4).

Meanwhile, the two protein variants, only one of phenylalanine 19 and isoleucine 32 of which was substituted with asparagine, had no effect of delaying fibrosis, unlike the case in which the two amino acids were substituted therewith. This means that at least two amino acids among amino acids consistent with the result of the simulation method performed in Example 1 above should be substituted in order to effectively delay fibrosis of amyloid beta protein.

Example 3: Determination of Changes in Shape, Length and Cytotoxicity of Fibrils During Fibrosis of Amyloid Beta (1-42) Depending on Ratio of Protein Variant in Combination of Wild-Type and Protein Variant that Succeeded in Inhibiting Fibrosis The effect of the mutation (variation) on the fiber formation rate and the effect of a combination of the protein variant of the present invention and the wild-type amyloid beta protein were sequentially determined. Three species, namely, F19N/I32N, F19N/I32N/L34N, and F19N/I32N/A42N were selected from the protein variants that inhibited fibrosis in order to minimize the number of mutations and then the kinetic behaviors of the combination were observed for 24 hours.

The result showed that all of the three protein variants inhibited fibrosis of wild-type amyloid beta protein and the inhibitory effect thereof was dependent on the ratio of the wild-type and variant proteins. Specifically, when the F19N/I32N protein variants were present at 20%, 50%, and 100%, respectively, the ThT fluorescence intensity was decreased by 67%, 52%, and 15%, compared to when the pure wild-type mutant was considered 100%.

It was found that the fibrils were also reduced on the TEM image and the average fiber lengths were 386.3 nm, 495.5 nm, and 742.7 nm, respectively, when the ratios of protein variants were 20%, 50%, and 100%. This showed that the fiber length of the wild-type amyloid beta protein was 334.5 nm, whereas the protein variant of the present invention had an increased fibril length and has a mixed distribution from short fibrils to very long fibrils. Based thereon, it could be predicted that fiber nucleation was disturbed and the protein variant interacted with wild-type amyloid beta protein to delay fiber nucleation.

Then, the cytotoxicity of the formed amyloid fibrils was compared to determine change in cytotoxicity of the amyloid beta (1-42) protein. Specifically, 15,000 cultured neuroblastoma were added with each of 1 uM of a monomer protein and 1 uM of a fibrous protein, and incubated for 2 days, and then the change in cytotoxicity was measured using MTT reagent.

As a result, as can be seen from FIGS. 3A to 3G, the viability of cells treated with fibrils of wild-type amyloid beta (1-42) was 63%, whereas the cell viability of a combination of the fibrils of wild-type amyloid beta with 20% of the protein variant of the present invention was increased to 72%, and in particular, the cell viability was increased to 76% when the ratio of the protein variant was increased to 50% (FIGS. 3A to 3G).

This is higher than the cell viability when the concentration of wild-type amyloid beta was reduced to 80%. This result indicates that the increase in cell viability is due to the interaction between the protein variant and the wild-type protein beyond the effect of simply reducing the concentration of the wild-type amyloid beta protein.

These results suggest that the protein variant of the present invention can prevent and/or treat neurodegenerative diseases such as Alzheimer's disease by increasing the viability of neuroblasts through interaction with wild-type amyloid beta protein.

Overall, it can be seen from the above examples that the structure-based protein variant of amyloid beta (1-42) that causes amyloid fibrosis delays fibrosis, which is a characteristic of wild-type amyloid beta, and also reduces cytotoxicity that occurs during amyloid fibrosis.

In addition, it can be seen that, unlike the conventional method for inhibiting amyloid fibrosis, according to the present invention, the formation rate and length of amyloid fibrils can be controlled through point mutants of amyloid beta protein, rather than using external additives such as antibodies and nanoparticles.

According to the present invention, fibrosis can be inhibited by kinetically delaying the fibril formation of amyloid beta (1-42) protein through point mutants designed based on the understanding of the structure and dynamics of the protein, and fibrosis can be delayed and the cytotoxicity of fibrils can be reduced through interaction of point mutants with wild-type amyloid beta (1-42).

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying filed claims and equivalents thereto rather than the Detailed Description of the Invention.

What is claimed is:

1. A protein variant comprising SEQ ID NO:1 with amino acid substitutions at positions 19 and 32 from the N-terminus of SEQ ID NO: 1, wherein the amino acid substitution at positions 19 and 32 is identical to each other, wherein the amino acid substitution is for asparagine (N), glutamine (Q), serine (S) or threonine (T), and wherein the protein variant optionally has up to two additional amino acid substitutions at positions 34 and 42 as compared to SEQ ID NO: 1.

2. The protein variant according to claim 1, wherein the protein variant has inhibited amyloid beta fibrosis compared to a wild-type protein.

3. The protein variant according to claim 1, wherein the amino acid substitution is for asparagine (N).

4. The protein variant according to claim 1, wherein at least one of amino acids at positions 34 and 42 from the N-terminus of SEQ ID NO: 1 is substituted with another amino acid.

5. The protein variant according to claim 1, wherein the protein variant comprises an amino acid sequence selected from the group consisting of SEQ ID NOS: 2 to 8.

6. A polynucleotide encoding the protein variant according to claim 1.

7. A vector comprising the polynucleotide according to claim 6.

* * * * *